US009269530B2

(12) United States Patent
Botman et al.

(10) Patent No.: US 9,269,530 B2
(45) Date of Patent: Feb. 23, 2016

(54) SYSTEM FOR IN SITU REACTIVATION OF FLUORESCENCE MARKER (71) Applicant: FEI Company, Hillsboro, OR (US)

(72) Inventors: Aurélien Philippe Jean Maclou Botman, Portland, OR (US); Cameron James Zachreson, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/496,555

(22) Filed: Sep. 25, 2014

(65) Prior Publication Data

US 2015/0028205 A1  Jan. 29, 2015

Related U.S. Application Data

(62) Division of application No. 13/770,765, filed on Feb. 19, 2013, now Pat. No. 8,872,105.

(51) Int. Cl.
*H01J 37/22* (2006.01)
*G01N 21/64* (2006.01)
*G01N 23/225* (2006.01)
*H01J 37/26* (2006.01)

(52) U.S. Cl.
CPC .............. *H01J 37/226* (2013.01); *G01N 21/64* (2013.01); *G01N 21/6458* (2013.01); *G01N 23/225* (2013.01); *G01N 23/2251* (2013.01); *H01J 37/228* (2013.01); *H01J 37/26* (2013.01); *G01N 2021/6439* (2013.01)

(58) Field of Classification Search
CPC ....... H01J 37/226; H01J 37/228; H01J 37/26; H01J 2237/006; H01J 2237/2067; H01J 2237/31745; G01N 21/64; G01N 21/6458; G01N 23/225; G01N 23/2251; G01N 2021/6439
See application file for complete search history.

(56) References Cited

U.S. PATENT DOCUMENTS

| 5,479,024 A | 12/1995 | Hillner et al. |
| 5,811,804 A | 9/1998 | Van Blitterswijk et al. |
| 5,851,413 A * | 12/1998 | Casella et al. ................. 216/92 |

(Continued)

FOREIGN PATENT DOCUMENTS

| DE | 4233686 A1 | 4/1994 |
| FR | 2596863 A1 | 10/1987 |
| WO | WO2012038484 | 3/2012 |

OTHER PUBLICATIONS

Egerton, R.F., et al., "Radiation damage in the TEM and SEM" Micron 35 (2004) 399-405.*

(Continued)

*Primary Examiner* — Wyatt Stoffa
(74) *Attorney, Agent, or Firm* — Scheinberg & Associates, PC; Michael O. Scheinberg; John E. Hillert (57) ABSTRACT

Vapor is provided locally at a sample surface to allow fluorescence of the fluorescent markers in a vacuum chamber. For example, a nanocapillary can dispense a liquid near a region of interest, the liquid evaporating to increase the vapor pressure near the fluorescent markers. The increase in vapor pressure at the fluorescent marker is preferably sufficiently great to prevent deactivation or to reactivate the fluorescent marker, while the overall pressure in the vacuum chamber is preferably sufficiently low to permit charged particle beam operation with little or no additional evacuation pumping.

18 Claims, 6 Drawing Sheets

(56) References Cited

U.S. PATENT DOCUMENTS

| | | | |
|---|---|---|---|
| 6,002,471 A | 12/1999 | Quake | |
| 6,259,104 B1 | 7/2001 | Baer | |
| 6,633,381 B2 | 10/2003 | Uhl | |
| 6,801,595 B2* | 10/2004 | Grodzins et al. | 378/45 |
| 7,317,515 B2* | 1/2008 | Buijsse et al. | 356/72 |
| 7,845,245 B2* | 12/2010 | Hayles et al. | 73/864.91 |
| 8,319,181 B2* | 11/2012 | Parker et al. | 250/307 |
| 8,431,896 B2* | 4/2013 | Mulders et al. | 250/309 |
| 2002/0053638 A1* | 5/2002 | Winkler et al. | 250/306 |
| 2004/0262515 A1* | 12/2004 | Motoi et al. | 250/306 |
| 2006/0098188 A1* | 5/2006 | Buijsse et al. | 356/72 |
| 2006/0197017 A1* | 9/2006 | Motoi et al. | 250/310 |
| 2008/0088831 A1* | 4/2008 | Mulders et al. | 356/237.2 |
| 2009/0000400 A1* | 1/2009 | Hayles et al. | 250/306 |
| 2010/0067102 A1* | 3/2010 | Yokoi et al. | 359/385 |
| 2010/0197039 A1* | 8/2010 | Zang et al. | 436/172 |
| 2010/0320381 A1 | 12/2010 | Zhao | |
| 2011/0070381 A1* | 3/2011 | Toth et al. | 427/585 |
| 2011/0203931 A1* | 8/2011 | Novosselov et al. | 204/600 |
| 2011/0226819 A1* | 9/2011 | Mulders et al. | 222/566 |
| 2013/0068611 A1* | 3/2013 | Botman et al. | 204/192.11 |
| 2014/0151335 A1* | 6/2014 | Botman et al. | 216/94 |
| 2014/0159860 A1* | 6/2014 | Lawandy | 340/5.8 |

OTHER PUBLICATIONS

Krishman, R.V. et al., "Fluorescence Methods to Probe Nanometer-Scale Organization of Molecules in Living Cell Membranes", Journal of Fluorescence, Sep. 3, 2001, pp. 211-226, vol. 11, No. 3.

* cited by examiner

Extinction of GFP fluorescence as a function of chamber pressure, and its reactivation upon venting

SYSTEM FOR IN SITU REACTIVATION OF FLUORESCENCE MARKER

This application is a divisional application of U.S. patent application Ser. No. 13/770,765, filed Feb. 19, 2013, which is incorporated by reference herein.

TECHNICAL FIELD OF THE INVENTION

The present invention relates to reactivation of fluorescent markers under reduced pressure conditions.

BACKGROUND OF THE INVENTION

Biological systems are extremely complex. Understanding them requires the ability to see detailed relationships between structure, function, and localization at various levels of resolution. A correlative approach, which uses both optical microscopy and electron microscopy produces the most comprehensive results. For example, light microscopy information can be used to identify areas of biological importance and their dynamics within a sample, and then electron microscopy can be used to resolve structural details within those areas after fixation and/or staining.

One powerful technique that has gained wide acceptance for research into cellular structure, molecular dynamics, and motility is the application of recombinant genetic techniques to link "reporter" genes to "genes of interest" (GoIs). Thus, when a particular GoI is expressed during normal genetic transcription/translation processes, the reporter gene will also be expressed, producing a small, detectable protein which ends up attached to the "protein of interest" (PoI) encoded for by the GoI.

A widely-accepted reporter gene is that encoding for a green fluorescent protein (GFP), these reporter genes being available in wild-type and genetically-modified versions, and the expressed GFPs having fluorescence that extends from blue to red in emission wavelengths. The GFP is relatively small (29.6 kDa, 3 nm in diameter by 4 nm long) with its chromophore well protected inside and not requiring any co-factors for light emission. In biological environments, all that is needed to "light up" a GFP is illumination by a laser at an appropriate wavelength for GFP excitation and fluorescent decay.

Clearly, if the X-Y-Z location of the GFP can be determined precisely within a cell (say, to 10 nm accuracy) then the location of the PoI would be known to a similar accuracy. The fluorescing GFP can be observed through a light microscope and so the location of the PoI can be seen relative to observable structures in the sample. An electron microscope, although unable to see the fluorescense, can then be used to form an image of the structure at a much higher magnification than is possible in a light microscope. Several techniques in the prior art have been proposed and, in some cases, demonstrated, for achieving high positional information from various fluorescent markers such as GFPs, dyes, and quantum dots. In one technique, proposed in U.S. Pat. No. 7,317,515 to Buijsse et al. for "Method of Localizing Fluorescent Markers," which is assigned to the assignee of the present application and which is hereby incorporated by reference, a charged particle beam would scan the surface of the sample, damaging the markers and extinguishing the fluorescence when the beam hits the fluorescent marker. The location of the fluorescent marker would then correspond to the position of the charged particle beam when the fluorescence is extinguished. Because the charged particle beam can be focused to a much smaller point than the laser that illuminates the marker, and the position of the charged particle beam at any time during its scan would be determined with great accuracy, the position of the fluorescent marker, and therefore the position of the PoI, would then be determined with similar accuracy.

SUMMARY OF THE INVENTION

It is an object of the invention, therefore, to improve imaging of structures using fluorescent markers in a vacuum chamber.

Applicants have discovered that some fluorescent markers stop fluorescing when exposed to a low pressure (sub-atmosphere) environment and that the fluorescence is restored when the fluorescent marker is brought back to a higher pressure.

Embodiments of the invention provide vapor locally at a sample surface to allow fluorescence of the fluorescent markers in a vacuum chamber. For example, a nanocapillary can dispense a liquid near a region of interest, the liquid evaporating to increase the vapor pressure near the fluorescent markers. The increase in vapor pressure at the fluorescent marker is preferably sufficiently great to prevent deactivation or to reactivate the fluorescent marker, while the overall pressure in the vacuum chamber is preferably sufficiently low to permit charged particle beam operation with little or no additional evacuation pumping.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF PREFERRED EMBODIMENTS

Applicants have discovered that some fluorescent markers stop fluorescing when exposed to a reduced pressure (sub-atmosphere) environment and that the fluorescence is restored when the fluorescent marker is brought back to a higher pressure.

Applicants provide vapor locally near the fluorescent markers to prevent deactivation or to reactivate the fluorescent markers in a vacuum chamber. In some embodiments, the fluorescent markers are reactivated without increasing the vacuum chamber pressure to a point at which a charged particle beam column becomes unusable. In some embodiments, the pressure in the vacuum chamber may temporarily rise above the operating pressure of a charged particle beam column, but the amount of vapor is relatively small and the chamber can be rapidly pumped back down to an operating pressure.

The invention facilitates correlative microscopy because the sample can be maintained in a vacuum system for electron microscopy and/or ion beam processing, yet can be analyzed by light microscopy using fluorescent markers without having to vent the vacuum chamber to the atmosphere. Maintaining the work piece in the vacuum chamber without venting facilitates rapid sequential operations using a charged particle beam and an optical microscope. For example, a portion of the work piece can be exposed using ion beam milling, fluorescent markers located using an optical microscope, and then imaged using an electron beam. This process can be repeated to sequentially expose multiple faces, which can be combined to form a three-dimensional image.

Throughout all descriptions herein of the present invention, the term GFP will be used to represent the larger class of fluorescent markers which may lose fluorescent properties in vacuum conditions, including GFPs, organics dyes, as well as inorganic markers such as quantum dots (which may typically be functionalized to enable selective attachment to particular intracellular components such as proteins, nucleic acids, etc.).

Figure 1:
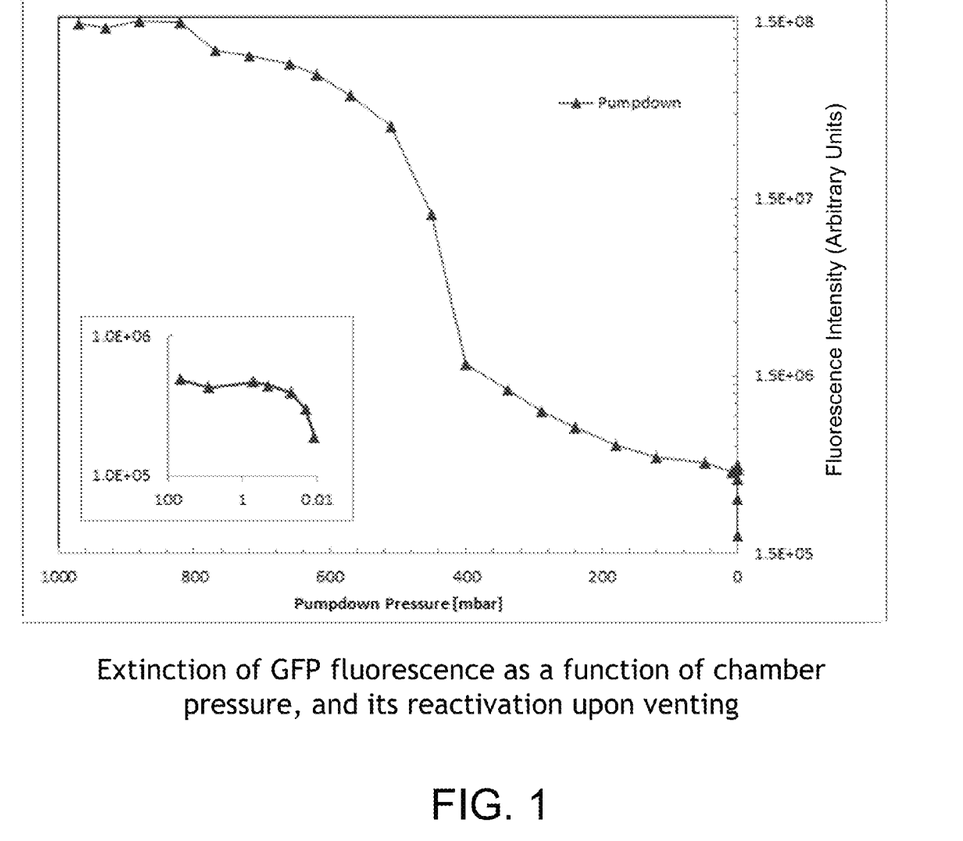
FIG. 1 is a graph showing fluorescent intensity versus vacuum chamber pressure.

FIG. 1 shows a graph of fluorescent intensity of green fluorescent proteins versus vacuum chamber pressure. The GFP were dried on a microscope slide and exposed to light with wavelength 385 nm at a nominal power of approximately 10 mW. FIG. 1 shows that as the pressure in the vacuum chamber decreases, the intensity of the fluorescence decreases. As the pressure decreases below about 400 millibar, the fluorescence decreases by two orders of magnitude compared to atmospheric pressure fluorescence. When the chamber is vented with room air, the fluorescence resumes.

Figure 2:
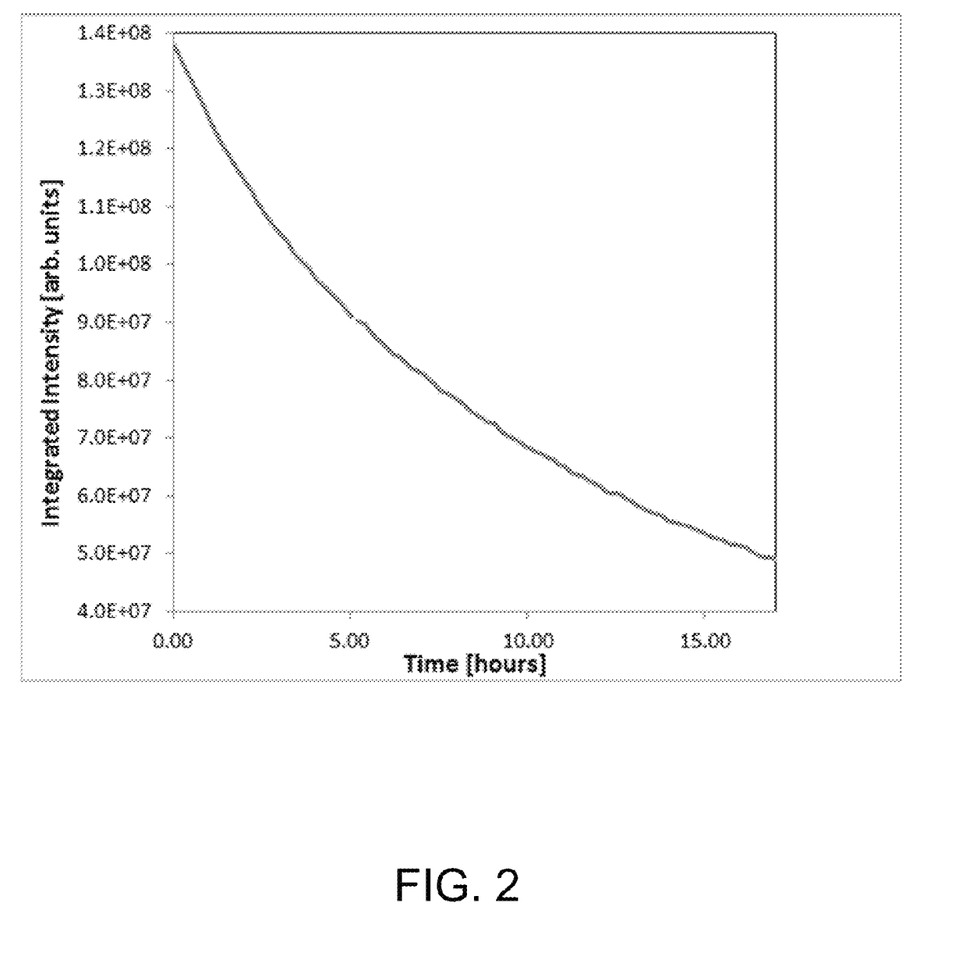
FIG. 2 is a graph showing the bleaching of fluorescent markers over time.

It is well known that many fluorescent markers are "bleached," that is, lose their fluorescence over time as they are exposed to light. FIG. 2 shows how the intensity of fluorescence decreases over time due to the bleaching using the same illumination conditions as used in the experiment for FIG. 1. FIG. 1, therefore, is a convolution of the decrease in fluorescence caused by bleaching and the decrease in fluorescence caused by the reduced vacuum pressure. To determine the decrease in fluorescence attributable to the vacuum, one would deconcolve the curve of FIG. 1 with the curve of FIG. 2. However, it is clear from FIG. 2 that over the timescale of the data presented in FIG. 1 and using these illumination conditions, bleaching is not significant compared to the observed decrease in fluorescence caused by the reduced vacuum pressure.

U.S. patent application Ser. No. 13/693,938, for "Microfluidics Delivery Systems," which is assigned to the assignee of the present invention and which is hereby incorporated by reference, describes methods and apparatuses for locally providing a small amount of fluid, particularly in an evacuated chamber. Microfluidics delivery systems can be used to locally supply a small amount of liquid in a vacuum chamber. As the liquid steadily evaporates, the vapor pressure rises locally. The rise in local vapor pressure can reactivate the fluorescent markers that were deactivated by the vacuum. In an equilibrium condition, liquid continually flows from the nanocapillary to replenish the bubble as liquid evaporates from the bubble. U.S. patent application Ser. No. 13/693,938 describes means for controlling the flow rate from the nanocapillary. The local vapor pressure will be related to the evaporation rate.

Figure 3:
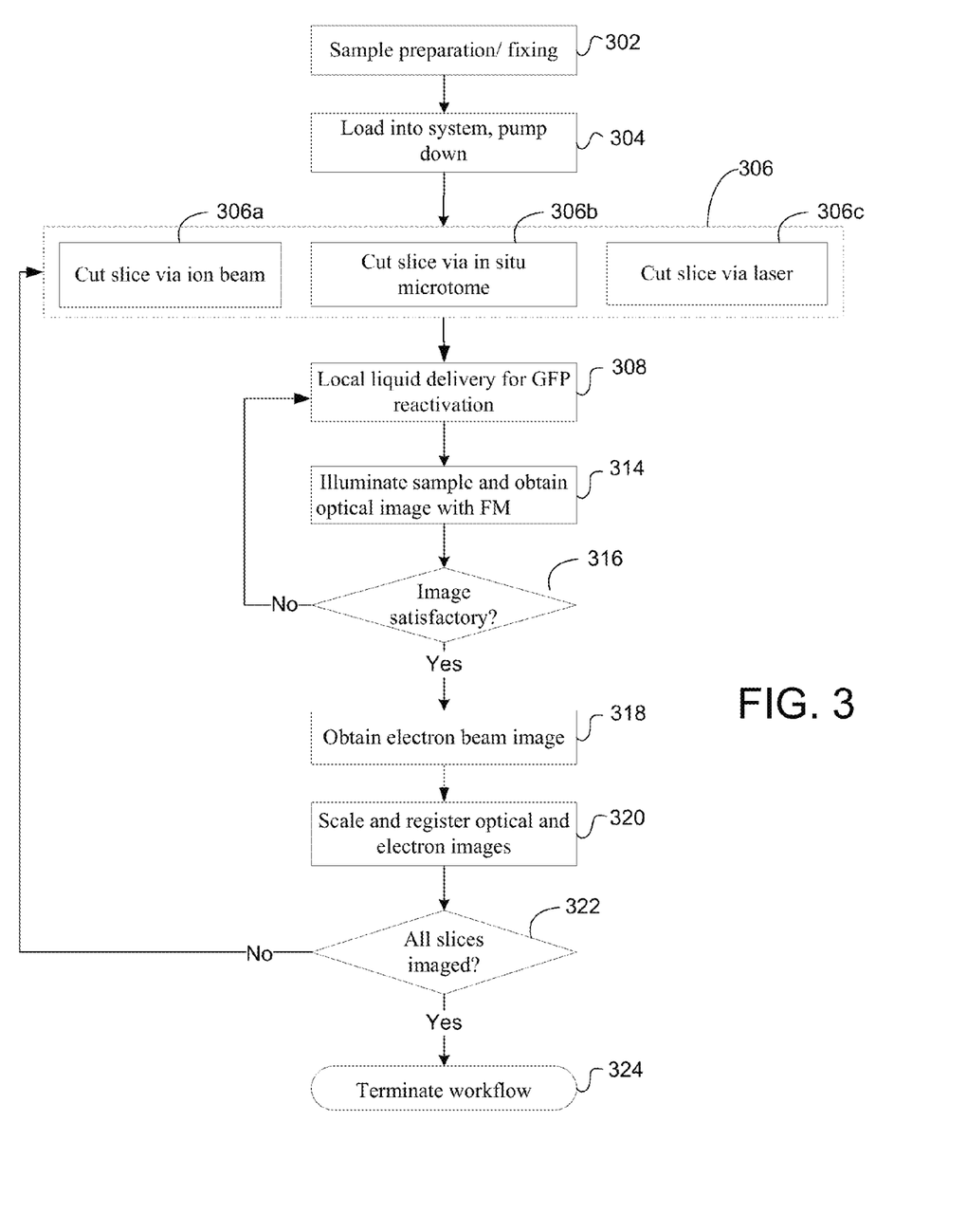
FIG. 3 is a flow chart showing the steps of an embodiment of the invention.

FIG. 3 shows a method of viewing multiple slices of a sample having fluorescent markers. In step 302, a biological sample having fluorescent markers is prepared or "fixed" to immobilize the molecules within the sample during imaging. The sample is fixed, for example, chemically or by freezing. In step 304, the sample is loaded into the vacuum chamber of a system including a charged particle beam column and an optical microscope. The system is configured to successively remove small layers of the sample to expose successive cross sections for imaging. The images of the multiple cross sections can be combined to produce a three-dimensional representation. In step 306, a surface of the sample is exposed by any method that does not damage fluorescent molecules located directly beneath the exposed surface. For example, in step 306a, a focused ion beam is directed toward the sample to remove material to expose a surface. Alternatively, in step 306b, the surface is exposed by using a microtome to slice material from the sample. In another alternative, as shown in step 306c, a laser removes material to expose a surface of the material. The laser can be, for example, an ultra-high speed pulsed laser, such as a femtosecond laser that removes material by ablation. In step 308, liquid is delivered to a region near the exposed surface. Liquid evaporates from the region near the exposed surface and raises the vapor pressure sufficiently to reactivate the fluorescent markers. For example, a nanocapillary can dispense water that evaporates to provide water vapor at the exposed surface. The size of the opening in the nanocapillary, the vacuum pressure and the temperature determine the equilibrium evaporation rate, which determines the vapor pressure at the exposed surface.

Figure 4:
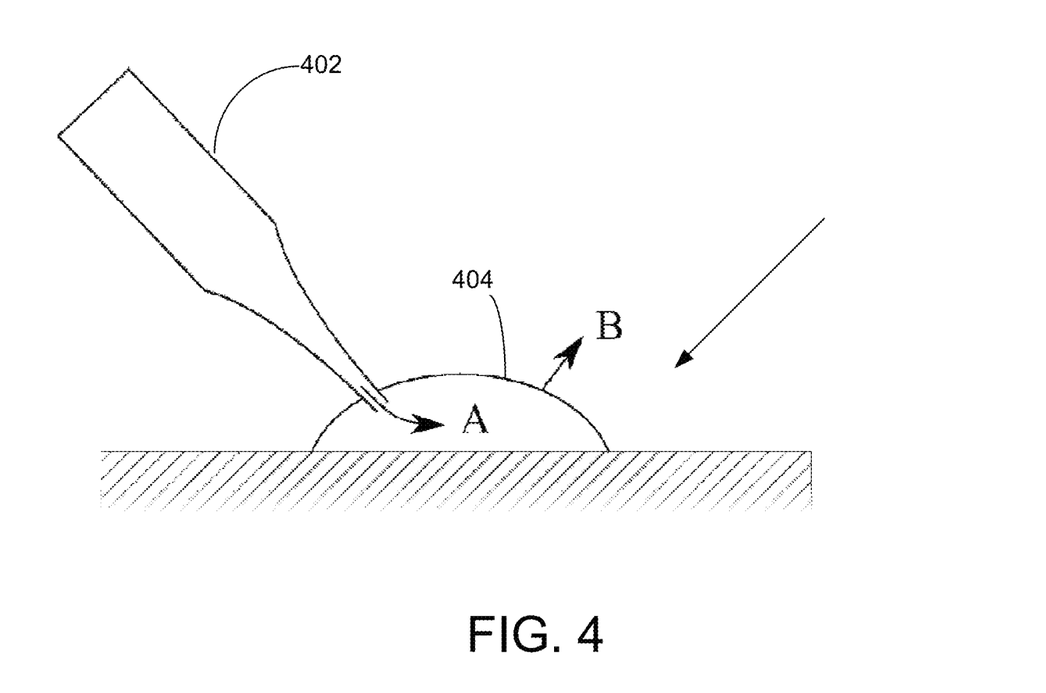
FIG. 4 shows schematically a drop formed on a surface by a nanocapillary.
Figure 5:
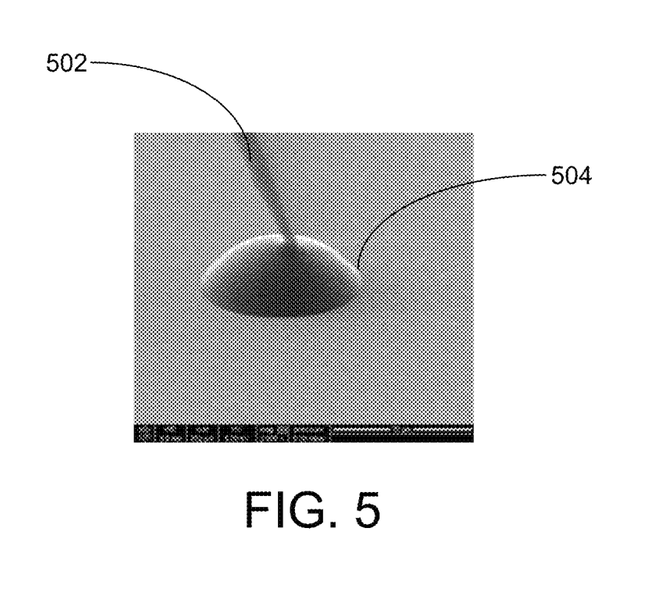
FIG. 5 is a photomicrograph showing a drop formed by a nanocapillary.

FIG. 4 shows schematically the process in which liquid leaves nanocapillary 402 to form a drop 404 while vapor evaporates from the drop 404. As described in U.S. patent application Ser. No. 13/693,938, at equilibrium, the size of the drop remains about the same, with liquid indicated by "A" flowing into the drop at the same rate that vapor indicated by "B" leaves the drop. FIG. 5 shows an image of a nanocapillary 502 and a drop 504.

As described in U.S. patent application Ser. No. 13/693, 938, a channel can be formed to completely or partially surround a region of interest to lead the liquid from the nanocapillary to the region of interest in order to maintain a higher vapor pressure in the region of interest. The nanocapillary can contact the work piece surface to initiate the liquid flow before optical imaging. After optical imaging, the nanocapillary can then be lifted from the surface to stop the flow. The nanocapillary exit diameter is preferably sufficiently small, that liquid flows by capillary action. When the contact between the nanocapillary and the surface is broken, the liquid will stop flowing. The drop on the surface will then evaporate, with the vapor diffusing through the vacuum chamber. This will reduce the gas pressure near the region of interest to improve charged-particle beam imaging when the fluorescent markers are not being imaged.

In a preferred embodiment, the background pressure in the vacuum chamber away from the sample face preferably remains below about $1 \times 10^{-3}$ millibar, while the local partial pressure at the exposed face is preferably greater than about $1 \times 10^{-2}$ millibar. More preferably, the background pressure in the vacuum chamber remains below about $1 \times 10^{-4}$ millibar, while the local partial pressure at the exposed face is greater than about $1 \times 10^{-2}$ millibar. The vapor pressure at the sample face should be sufficient to reactivate or maintain activation of the fluorescent markers and the required pressure will depend on the fluorescent markers and sample preparation. The background pressure in the vacuum chamber is preferably sufficiently low to allow operation of the charged particle beam and will depend on the charged particle beam column design and operating parameters.

In step 314, the sample is exposed to illuminating radiation that excites the fluorescent markers and an optical image of the sample with the fluorescent markers is recorded. In decision block 316, the user determines whether or not the optical image is satisfactory. If the image is not satisfactory, the vapor pressure at the exposed surface is increased. For example, a larger nanocapillary may be used, the temperature of the nanocapillary can be raised, the temperature of the sample can be raised (to increase flow out of the nanocapillary) or cooled (to reduce evaporation from the dispensed fluid), the position of the nanocapillary relative to the surface can be changed, or the pressure in the vacuum chamber may be increased.

If the optical image with the fluorescent markers is satisfactory, then an electron beam image of the exposed face is obtained in step 318. This is typically a scanning electron microscope image, in which the electron beam scans across the exposed face, and secondary electrons are collected. The brightness of the points on the image correspond to the number of secondary electrons detected. In step 320, a portion of the optical image and the electron beam image are converted to a similar scale and registered to each other so that features of both images can be seen on a combined image. The optical image gives information regarding the position of the GFPs and hence of the features of interest (for example, the GoI), while the electron beam provides high resolution images containing information not readily obtainable with the optical method. The two images may be combined into one image, viewed separately, or combined by modulating the relative contrast present in each image.

After the electron beam image is obtained, the process returns to step 306 in which material is removed from the previously exposed face of the sample to expose a new face. The process is repeated until it is determined in decision block 322 that all the desired images are collected and the process terminates in block 324. By collecting images at different depths into the sample, a three-dimensional representation of the sample can be constructed.

In each exposed face, the liquid from the nanocapillary provides locally delivered vapor that either prevents the fluorescent markers in the surface from being exposed to a vacuum and deactivating, or reactivates the exposed surface if the fluorescent markers have already been deactivated.

As shown in FIG. 1, in the specific instance of these GFPs illuminated at the experimental conditions and maintained at the temperature set by the experimental conditions, to reactivate the fluorescent markers, the pressure needs to be fairly high, higher than about 400 mbar to obtain a detectable excitation with the collection optics used. This pressure threshold depends on the efficiency of the collection optics, the amount of GFPs present and fluorescing, the temperature of the sample, the strength of the exciting illumination, and other experimental conditions. Regardless of the specific conditions, the pressure required to obtain the excited fluorescence is significantly higher than pressures typically compatible with long mean free paths of electrons typically required for electron microscopy. While venting the vacuum chamber could be done between each slice to obtain an optical image using the fluorescent markers, venting and re-evacuating the vacuum chamber between each slice would be very time consuming. In the case of using an Environmental Scanning Electron Microscope (ESEM) where water vapor can be brought into the chamber at comparatively high pressure while still being able to scan with the electron beam, such high pressures are not compatible with high resolution electron beam imaging, so the pump and vent time involved in switching between high vacuum and ESEM mode would also be unacceptably long. Additionally, pumping and venting may also irreversibly denature GFPs in the bulk sample that have not been imaged yet. Embodiments of the present invention obviate the need for venting and re-evacuating by providing a local region of high pressure that dissipates rapidly to allow charged particle beam operations for slicing or imaging while keeping the total analysis time to reasonable durations.

While the process described above uses a nanocapillary dispensing a liquid product to produce vapor locally, other embodiments may increase the pressure around the sample using different techniques. For example, a gas injection system, such as one described in U.S. Prov. Pat. App. No. 61/677,226 for an "Environmental SEM Gas Injection System" or in U.S. Pat. No. 5,435,850 for a "Gas Injection System," can be used. In other embodiments, pressure around the sample can be increased by increasing the pressure in the vacuum chamber, decreasing the sample temperature, or by operating within an environmental cell at higher pressure within the vacuum chamber, although such a system may require excessive time to evacuate after viewing to resume high vacuum mode for charged particle beam operation.

Figure 6:
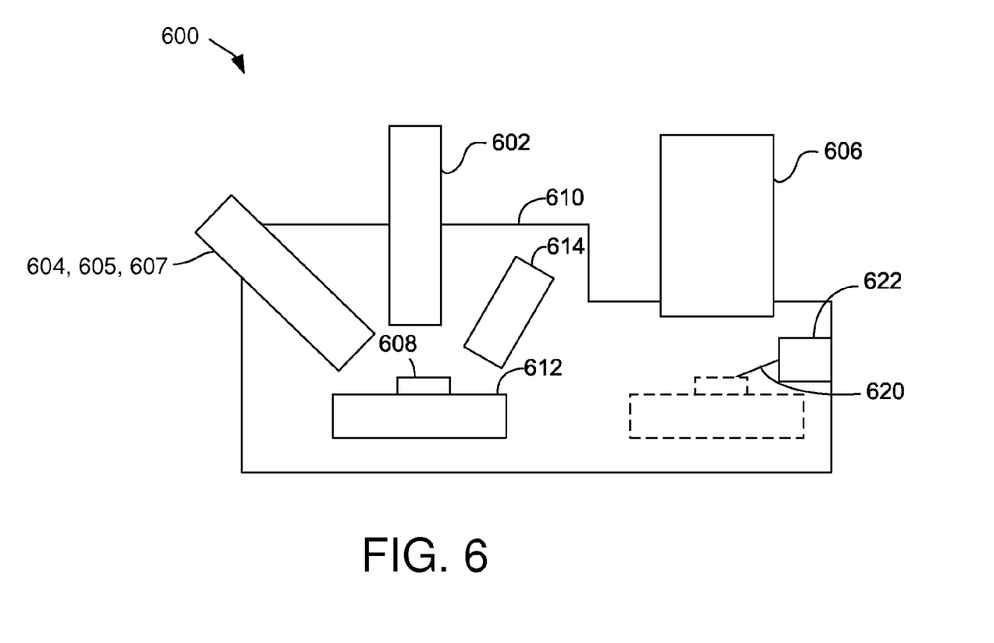
FIG. 6 shows schematically a dual beam system including an ion beam column, an electron beam column, and an optical microscope.

Because a liquid delivery system is easily added to an existing system, embodiments of the invention can be implemented in existing systems that include a focused ion beam column for milling material to expose new faces and an electron beam column for scanning electron microscopy or backscatter electron imaging. FIG. 6 shows such a system schematically.

The dual beam system 600 includes an electron beam column 602 oriented vertically; a focused ion beam column 604 tilted at approximately 52 degrees from the vertical or, in alternative embodiments, a laser 605 or a microtome 607; and optical microscope 606. A sample 608 in vacuum chamber 610 is mounted on a sample stage 612 that can preferably move in three directions and can also rotate and tilt. A secondary electron detector 614 detects secondary electrons generated by the impact on the sample of an ion beam from ion column 604 or by the impact of electrons from electron beam column 602. In the embodiment shown, the electron beam column 602 and the ion beam column 604 produce beams that are coincident, that is, they impact at approximately the same spot on the sample 608. The field of view of the optical microscope is away from the impact point of the beams and the sample stage moves the sample between the viewing area of the optical microscope and the operating area of the charged particle beams. A nanocapillary 620 mounted on a micromanipulator 622 is positioned by the optical microscope so that the nanocapillary can be moved into contact with the sample surface to provide liquid flow onto the surface to provide vapor to reactivate the fluorescent markers in the sample.

The configuration of the columns may be different in different embodiments. For example, in some embodiments, both the ion beam column and the electron beam column are tilted from the vertical. In some embodiments, the field of view of the optical microscope overlaps the impact point of the charged particle beams, that is, the two beams and the optical microscope are coincident. For example, an ion beam column may be located in a plane normal to the plane containing an electron beam column, with both columns being oriented approximately 45° from the vertical. The sample can be illuminated and light collected vertically from above. Alternatively, an optical column can be in the same plane as one of the charged particle beam columns.

Figure 7:
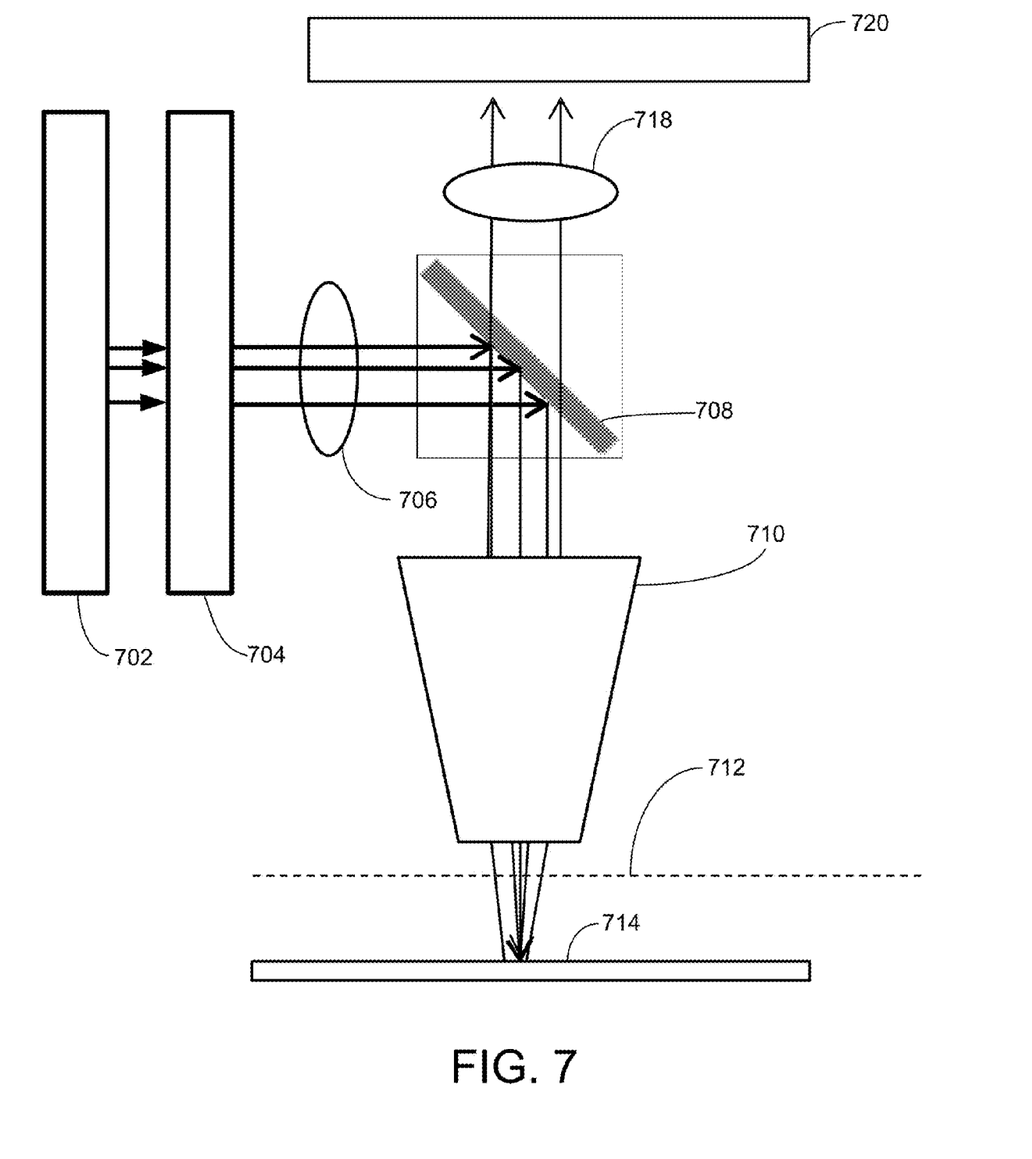
FIG. 7 shows an optical microscope for illuminating and viewing fluorescent markers.

FIG. 7 shows a typical optical microscope in more detail. A source 702 of illuminating radiation provides light through an optical fiber 704, the light passing through a 385 nm bandpass filter 706 and being reflected by a dichoric mirror 708 through an objective lens 710 and a vacuum chamber window 712 toward the sample 714. The illumination causes the fluorescent marker in the sample to fluoresce. The light from the sample passes back through the vacuum chamber window 712, the objective lens 710, the dichoric mirror 708, and through a bandpass filter 718 to a detector 720, which forms an image using the light from the fluorescent markers. Bandpass filter 718 prevents light from source 702 from reaching detector 720.

It will be understood that the magnification of the optical image will be less than the magnification of the electron beam image. Techniques for scaling and aligning the images are well known in correlative microscopy so that structures identified using the fluorescent markers can then be examined in an electron beam image.

Although the present invention and its advantages have been described in detail, it should be understood that various changes, substitutions and alterations can be made herein without departing from the spirit and scope of the invention as defined by the appended claims. The scope of the present application is not limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein, may be utilized according to the present invention. Accordingly, the appended claims are intended to include within their scope such processes, machines, manufacture, compositions of matter, means, methods, or steps.

We claim as follows:

1. A system for analyzing a specimen, comprising:
a vacuum chamber;
an electron beam column for scanning a focused electron beam over a surface of a sample in the vacuum chamber;
an electron detector for detecting secondary electrons emitted from the sample in response to an impact of the electron beam to form an image of the sample;
an optical system for illuminating the sample within the vacuum chamber with a wavelength of light that causes fluorescence of fluorescent markers in the sample and for detecting fluorescence from the fluorescent markers; and
a nanocapillary that dispenses a liquid that evaporates, the nanocapillary configured for locally applying vapor to the surface of the sample at pressures sufficient to increase an activity of the fluorescent markers while maintaining a lower background pressure in the vacuum chamber.

2. The system of claim 1 further comprising a focused ion beam column for processing the sample.

3. The system of claim 1 further comprising a laser for processing the sample.

4. The system of claim 1 further comprising a microtome for processing the sample.

5. The system of claim 1 further comprising a heater capable of heating the sample to hotter than 60 °C.

6. The system of claim 1 further comprising a cooler capable of cooling the sample to cooler than −20 °C.

7. The system of claim 1 wherein an operating pressure in the chamber is less than $1\times10^{-4}$ millibar.

8. The system of claim 1 wherein a local pressure due to the locally applied vapor is greater than $1\times10^{-2}$ millibar while the background chamber pressure is less than $5\times10^{-3}$ millibar.

9. The system of claim 1 in which the nanocapillary has a diameter of less than 20 μm.

10. The system of claim 1 further comprising a channel configured to transport the liquid from the nanocapillary to a region of interest on the surface of the sample.

11. The system of claim 1 in which the nanocapillary is configured to:
cause a flow of the liquid towards the surface of the sample before the optical system carries out an optical imaging of the sample by making contact with the surface of the sample such that nanocapillary action induces the flow of the liquid; and
stop the flow of the liquid by breaking contact between the nanocapillary and the surface of the sample after the optical system carries out the optical imaging of the sample.

12. The system of claim 1 in which the nanocapillary is configured to completely or partially surround a region of interest on the surface of the sample.

13. The system of claim 1 in which the system is configured to:
successively remove small layers of material from the sample to expose successive cross-sections of the sample for imaging; and
produce a three-dimensional representation of the sample by combining images of the successive cross-sections.

14. The system of claim 13 in which the system is configured to utilize a focused ion beam, a laser, or a microtome to successively remove the small layers of material.

15. The system of claim 1 in which the fluorescent markers comprise a green fluorescent protein that loses fluorescent properties in vacuum conditions.

16. The system of claim 1 in which the sample is produced from a gene of interest linked to a reporter gene encoded to produce green fluorescent protein.

17. A system for analyzing a specimen, comprising:
a vacuum chamber;
an electron beam column for scanning a focused electron beam over a surface of a sample in the vacuum chamber;
an electron detector for detecting secondary electrons emitted from the sample in response to an impact of the electron beam to form an image of the sample;
an optical system for illuminating the sample within the vacuum chamber with a wavelength of light that causes fluorescence of fluorescent markers in the sample and for detecting fluorescence from the fluorescent markers; and
a source of water vapor for locally applying vapor to the surface of the sample at pressures sufficient to increase an activity of the fluorescent markers while maintaining a lower background pressure in the vacuum chamber, and
in which:
the optical system is configured to record an optical image of a face of the sample after exposing the face to an illuminating radiation that causes the markers to fluoresce;
the electron beam column is configured to capture an electron beam image of the face after the optical image is recorded; and the system is configured to convert a portion of the optical image and the electron beam image to a similar scale and to register the optical image to the electron beam image such that features of the optical image and the electron beam image can be seen on a combined image.

18. A system for analyzing a specimen, comprising:

a vacuum chamber;

an electron beam column for scanning a focused electron beam over a surface of a sample in the vacuum chamber;

an electron detector for detecting secondary electrons emitted from the sample in response to an impact of the electron beam to form an image of the sample;

an optical system for illuminating the sample within the vacuum chamber with a wavelength of light that causes fluorescence of fluorescent markers in the sample and for detecting fluorescence from the fluorescent markers; and a source of water vapor configured for locally applying vapor to the surface of the sample at pressures sufficient to increase an activity of the fluorescent markers while maintaining a lower background pressure in the vacuum chamber, the system configured to:

raise a vapor pressure near a region of interest comprising the fluorescent markers sufficient to prevent deactivation or to cause reactivation of the fluorescent markers; and optically image the region of interest using the optical system after raising the vapor pressure.

* * * * *